(12) United States Patent
Bouthillier (10) Patent No.: US 11,202,573 B2
(45) Date of Patent: Dec. 21, 2021

(54) SYSTEM AND METHOD FOR CAPTURING HIGH RESOLUTION COLOR VIDEO IMAGES OF THE SKIN WITH POSITION DATA

(71) Applicant: Design Net Technical Products, Inc., Smithfield, RI (US)

(72) Inventor: Robert J. Bouthillier, Smithfield, RI (US)

(73) Assignee: Design Net Technical Products, Inc., Smithfield, RI (US)

(*) Notice: Subject to any disclaimer, the term of this patent is extended or adjusted under 35 U.S.C. 154(b) by 591 days.

(21) Appl. No.: 15/448,684

(22) Filed: Mar. 3, 2017

(65) Prior Publication Data

US 2017/0251925 A1  Sep. 7, 2017

Related U.S. Application Data

(60) Provisional application No. 62/303,535, filed on Mar. 4, 2016.

(51) Int. Cl.
*A61B 5/00* (2006.01)

(52) U.S. Cl.
CPC ............ *A61B 5/0077* (2013.01); *A61B 5/441* (2013.01); *A61B 5/742* (2013.01); *A61B 2560/0431* (2013.01)

(58) Field of Classification Search
CPC ...... A61B 5/0077; A61B 5/0059; A61B 5/445
See application file for complete search history.

(56) References Cited

U.S. PATENT DOCUMENTS

| | | | | |
|---|---|---|---|---|
| 2005/0154381 A1* | 7/2005 | Altshuler | ............. | A61B 18/203 606/9 |
| 2007/0140427 A1* | 6/2007 | Jensen | ................... | A61B 6/481 378/98.12 |
| 2011/0184244 A1* | 7/2011 | Kagaya | .............. | A61B 1/00117 600/182 |
| 2017/0367580 A1* | 12/2017 | DiMaio | ................ | A61B 5/0064 |

* cited by examiner

*Primary Examiner* — Amelie R Davis
*Assistant Examiner* — John Denny Li
(74) *Attorney, Agent, or Firm* — Barlow, Josephs & Holmes, Ltd.; David R. Josephs (57) ABSTRACT

A system for capturing, storing and comparing dermatological images includes two components, namely, a handheld exam control and a patient interface. The handheld exam control includes a camera, display screen, illuminator and a position sensor. The patient interface includes a patient position template and a position sensor interface. The system captures an image sequence and the precise location of each image. Images may be compared to previous images by a clinician.

14 Claims, 7 Drawing Sheets

SYSTEM AND METHOD FOR CAPTURING HIGH RESOLUTION COLOR VIDEO IMAGES OF THE SKIN WITH POSITION DATA

CROSS-REFERENCE TO RELATED APPLICATION

This patent document claims priority to earlier filed U.S. Provisional Patent Application Ser. No. 62/303,535, filed Mar. 4, 2016, the entire contents of which are incorporated herein by reference.

BACKGROUND OF THE INVENTION

The present invention relates to an improved method and system for the acquisition of high-resolution video images of the skin, archiving and viewing of the video images, and a way to compare acquired images. More particularly, the present invention pertains to methods of using such a system to monitor skin conditions using previous images from a patient database to perform comparisons of the acquired image data.

In the field of dermatology, it is necessary to have a way by which to capture skin conditions and a way to monitor those conditions over time. Monitoring may be performed by a skilled professional using a careful procedure to evaluate skin surfaces by eye and may include capturing a series of photographs of specific regions. This helps to track changes to the skin for better diagnosis of any problems with the skin. A carefully planned and executed procedure is important when capturing photographs of the skin, as many factors may contribute to the way a still image appears; this is of particular interest when subsequent photos are captured and used for comparison. The existing art does not capture the position where a particular image was taken.

This system improves upon the prior art by combining a camera, illumination source, and position sensor to capture an image and know the precise and absolute position and scale of the image that was captured.

In view of the foregoing, there is a demand for a system and method that can precisely determine the absolute position of where an image was taken of the skin.

There is a demand for a system and method that can determine the scale of the image that was captured.

There is a demand or a system and method that can accurately track the changes to the condition of the skin over time for medical purposes.

SUMMARY OF THE INVENTION

To accomplish the features of the present invention there is provided an apparatus for capturing high-resolution images of the skin comprising: a patient interface and a handheld exam control which may be used by dermatologists or other medical professionals interested in capturing high-resolution images of skin surfaces; said handheld exam controller combining a fixed-focus camera with a laser projector and a wired or wireless position sensor, a way to synchronize laser projector illumination with camera frame-capture, a way to determine the absolute position of the camera, and a way to determine scale.

The present invention also relates to a way to retrieve a past skin image or images based on position data in a new capture, and a way to create a new skin capture based on position data in an existing image.

Therefore, an object of the present invention is to provide system and method that can precisely determine the absolute position of where an image was taken of the skin.

A further object is to provide a system and method that can determine the scale of the image that was captured.

Yet another object of the present invention is to provide a system and method that accurately tracks the changes to the condition of the skin over time for medical purposes.

BRIEF DESCRIPTION OF THE DRAWING FIGURES

Other objects, features and advantages of the invention shall become apparent as the description thereof proceeds when considered in connection with the accompanying illustrative drawings, in which.

DESCRIPTION OF THE INVENTION

By combining a camera, illumination source, and position sensor to capture images of the skin, the absolute position and the scale of a captured image can be determined with accuracy.

Figure 1A:
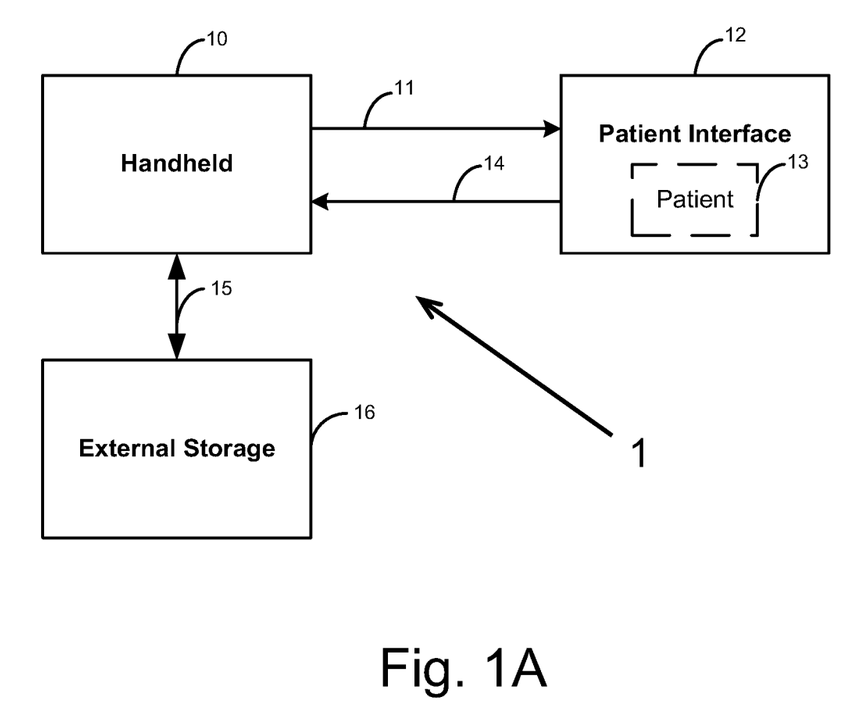
FIG. 1A is a system block diagram illustrating the DermaMap skin-mapping system.

FIG. 1A shows a top-level overview of the entire DermaMap system. The handheld exam control 10 is used to capture video images (frames) of a patient's skin to create a record of the condition of the skin and make it possible to track changes that may occur over time. The exam control captures images in a manner that synchronizes frame capture and laser illumination, while the patient 13 is situated on the patient interface 12 according to the patient image capture procedure. Communication occurs between the handheld exam control and the patient interface. Requests for position data 11 are sent from the handheld to the patient interface and responses containing the position data 14 are returned from the patient interface back to the exam control. The result of this communication is that the absolute position is reported and stored for each frame. A wired or wireless network 15 is used to send acquired images with position data to an external storage device 16. Stored images can be retrieved via a wired or wireless network 15 and position data can be accessed to capture new images of the exact same location on a patient's skin.

It should be understood that the position data collected and stored using known computer equipment that includes a microprocessor, memory, storage, I/O ports, power source and other components found in a computer device. The storage device may be a hard drive, solid state, optical drive or the like. The captured images and collected position data are accordingly stored in such storage device. The computer equipment may or may not be connected to a network, such as the Internet, to facilitate access and storage of the data therein.

Figure 1B:
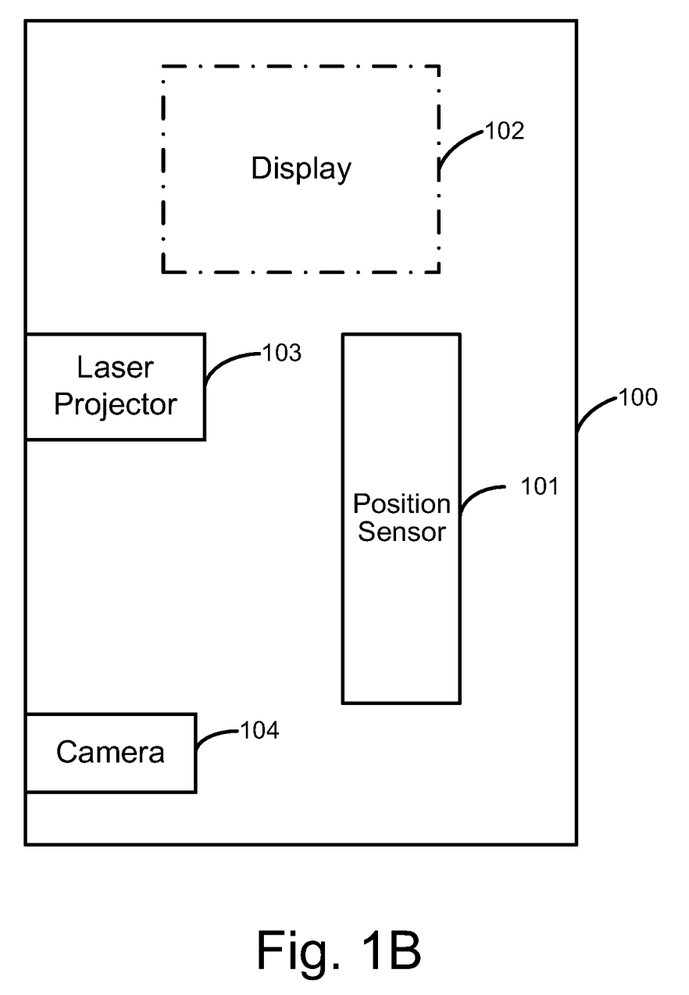
FIG. 1B is a block diagram illustrating the components of the Handheld Exam Control for the present invention.
Figure 2:
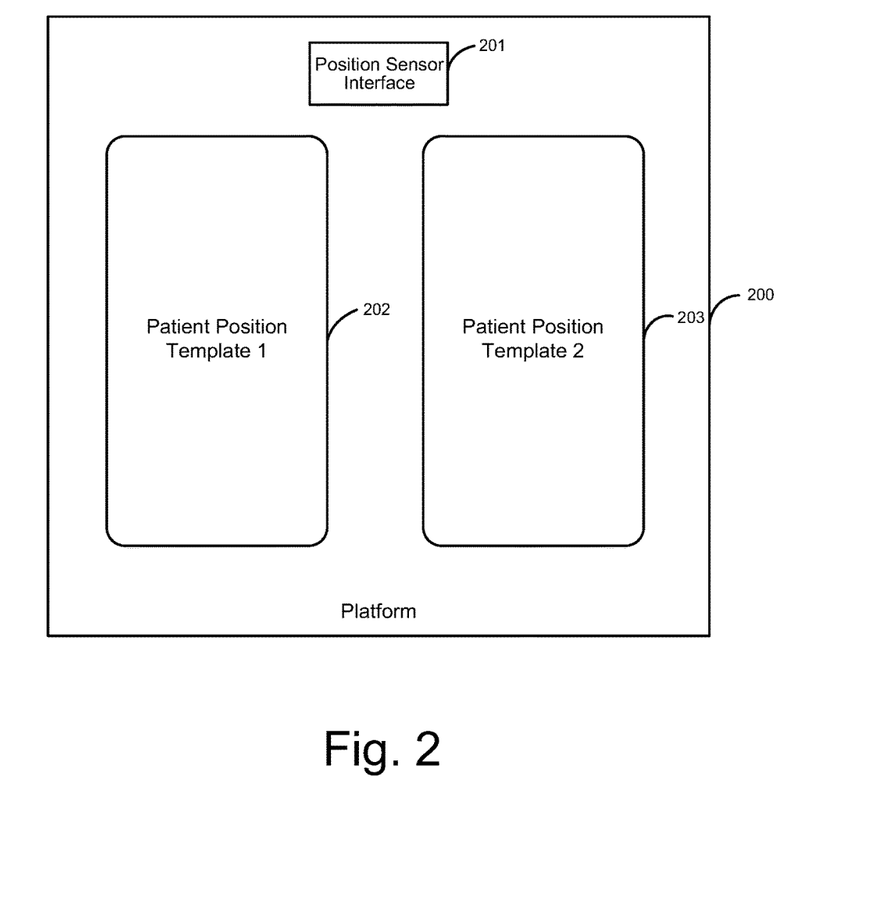
FIG. 2 is a block diagram illustrating the components of the Patient Interface for the present invention.

The handheld exam control, shown in FIG. 1B has a position sensor 101, display 102, laser projector (illumination source) 103 and a camera 104. The handheld exam control is used with the patient interface, representationally shown in FIG. 2. The patient interface has a support surface and a position sensor interface, 201, that communicates with the position sensor 101 on the exam control to determine the absolute position of captured images. The patient position templates 202 and 203 on a support surface of platform 200 are used to help position the patient for optimal image capture.

Figure 3:
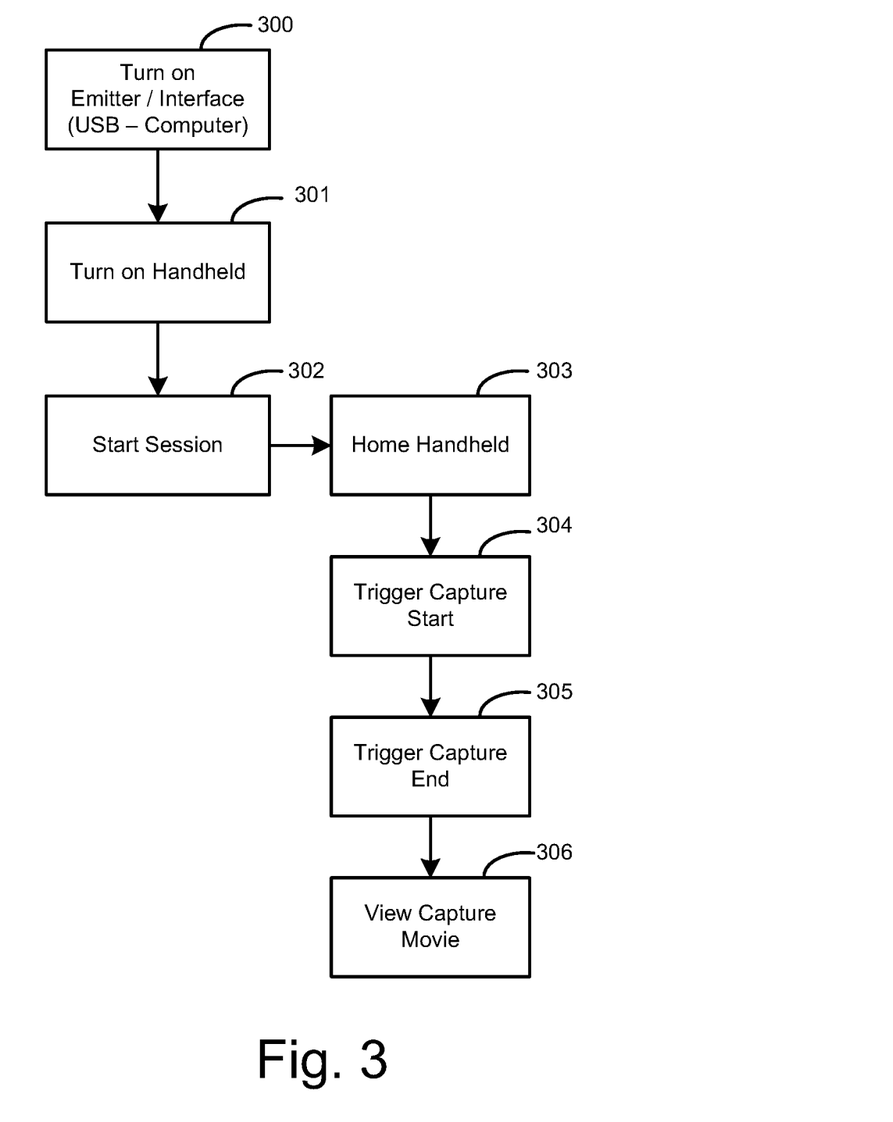
FIG. 3 is a flowchart illustrating an example of typical use of the DermaMap skin-mapping device.

FIG. 3 illustrates an overview of use of the skin-mapping device and system 1 of the present invention. The patient interface is turned on at step 300, activating the position sensor interface. At step 301, the handheld exam controller is turned on, activating the position sensor. At 302, the patient session begins. A patient session includes: homing the handheld exam controller at step 303; pressing the trigger to start capture at step 304; pressing the trigger a second time to end capture at step 305; and viewing the captured video at step 306.

Figure 4:
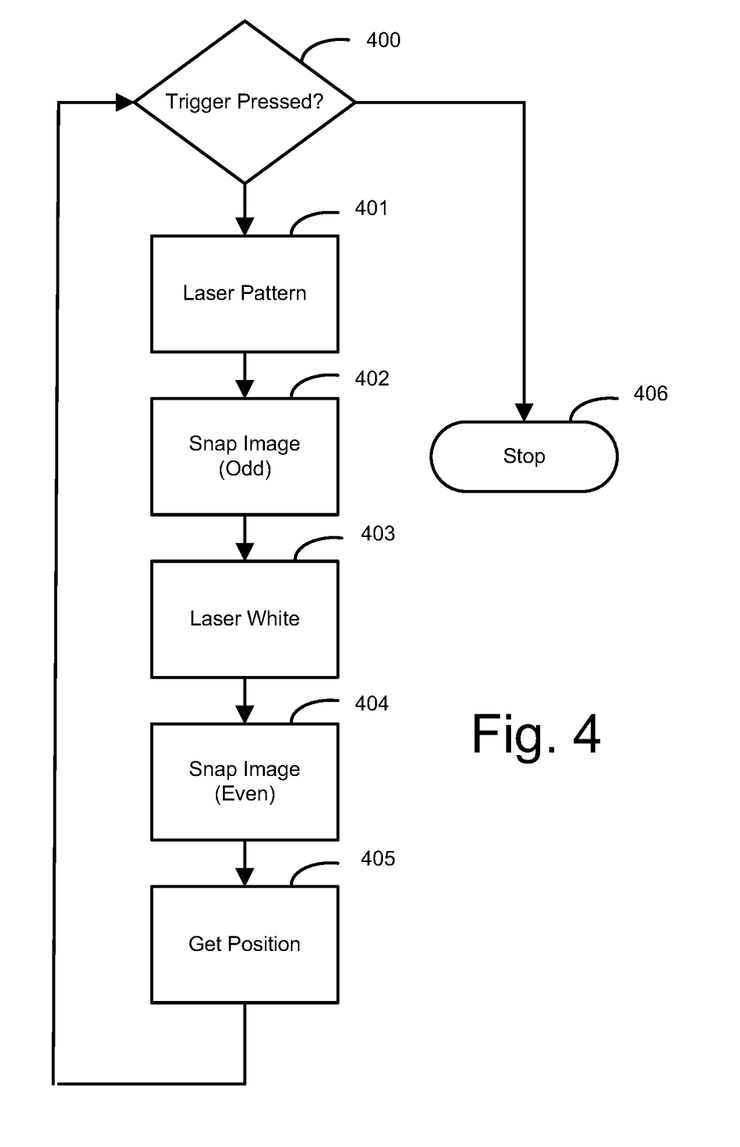
FIG. 4 is a flowchart illustrating a typical Capture sequence for the DermaMap skin-mapping device.

Turning now to FIG. 4, the capture sequence is initiated when the trigger is pressed in step 400. A laser (illumination) pattern is projected from the handheld exam control onto the patient's skin at step 401 and an odd video frame is captured at step 402. At step 403, an unpatterned colored light is projected from the handheld exam control onto the patient's skin and an even video frame is captured at step 404. At step 405, the position of the pair of captured images is recorded and save using the computer equipment. If the trigger is still pressed, the sequence will proceed and steps 401 through 405 will be repeated in sequence until the trigger on the handheld exam controller is up in the off position and the capture sequence ends at step 406.

Next, the camera is synchronized to the laser illumination source, the illumination pattern is always displayed on the skin when odd frames are captured and the colored illumination light is always displayed on the skin when even frames are captured. Captured video frames and absolute position data allow this data to be used after it is acquired. Images may be stored for comparison using computer software. The distance, perspective or angle, and camera rotation relative to the patient are all factors that need to be accounted for. The odd video frames, captured using an illumination pattern, can be used to determine this information. The size of elements in the pattern is used to determine the scale of the video and therefore determine the size of any skin lesions in the video.

Figure 5:
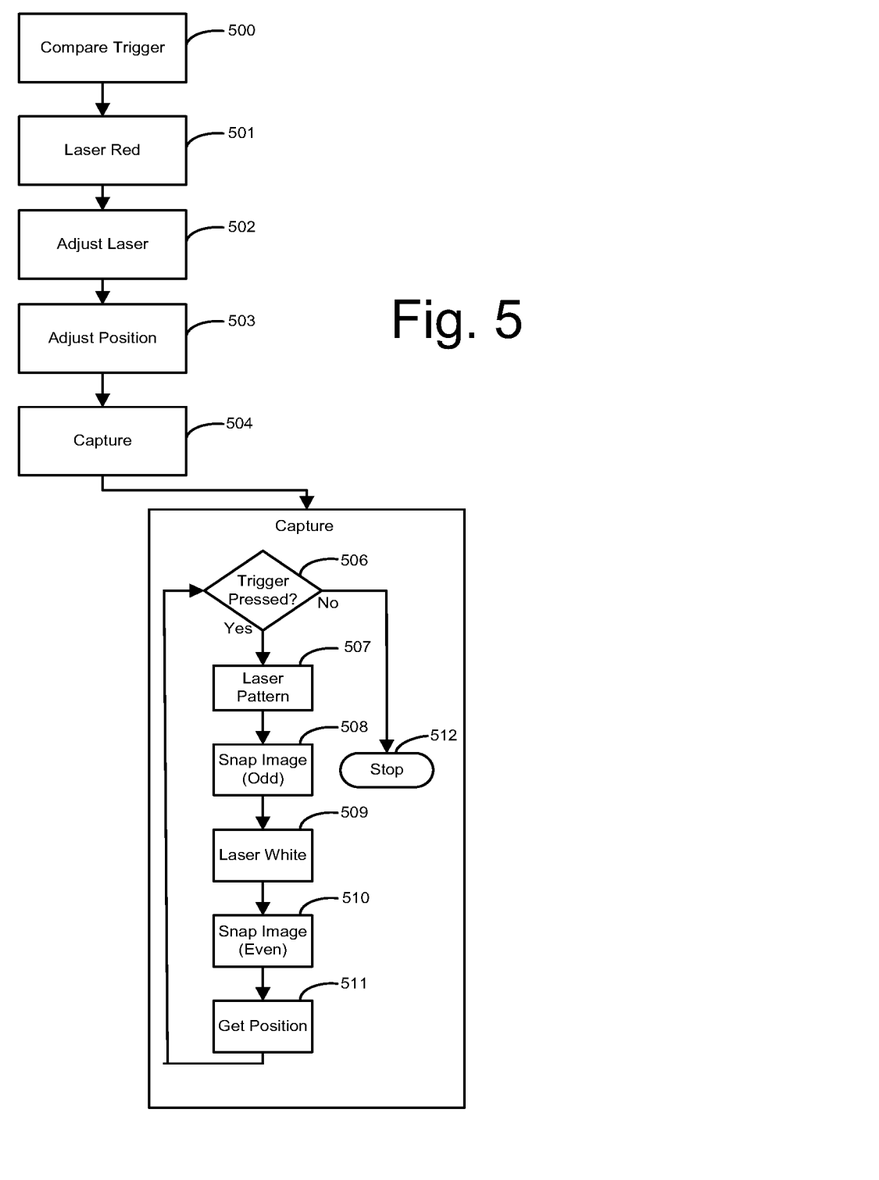
FIG. 5 is a flowchart illustrating an example of the Compare process for the DermaMap skin-mapping device.

FIG. 5 illustrates the compare function of the present invention. The compare function can be used to repeat an image capture using absolute position information from a previous image capture. In step 500, the trigger is pressed and the actual location is compared to the location in the previous image capture. In step 501, the unpatterned colored light is projected from the handheld exam control onto the patient's skin. In step 502, the laser pattern is projected onto a patient's skin and the actual distance between the handheld exam controller and the patient is compared to the image scale in the previous image capture. In step 503, the actual position is compared to the position location in the previous image capture and adjustments are made. In step 504, image capture takes place. When the trigger is pressed in step 506, a laser (illumination) pattern is projected from the handheld exam control onto the patient's skin at step 507 and an odd video frame is captured at step 508. At step 509, an unpatterned colored light is projected from the handheld exam control onto the patient's skin and an even video frame is captured at step 510. At step 511, the position of the pair of captured images is recorded. If the trigger is still pressed, the sequence will proceed and steps 507 through 511 will be repeated in sequence until the trigger on the handheld exam controller is up in the off position and the capture sequence ends at step 512.

Figure 6:
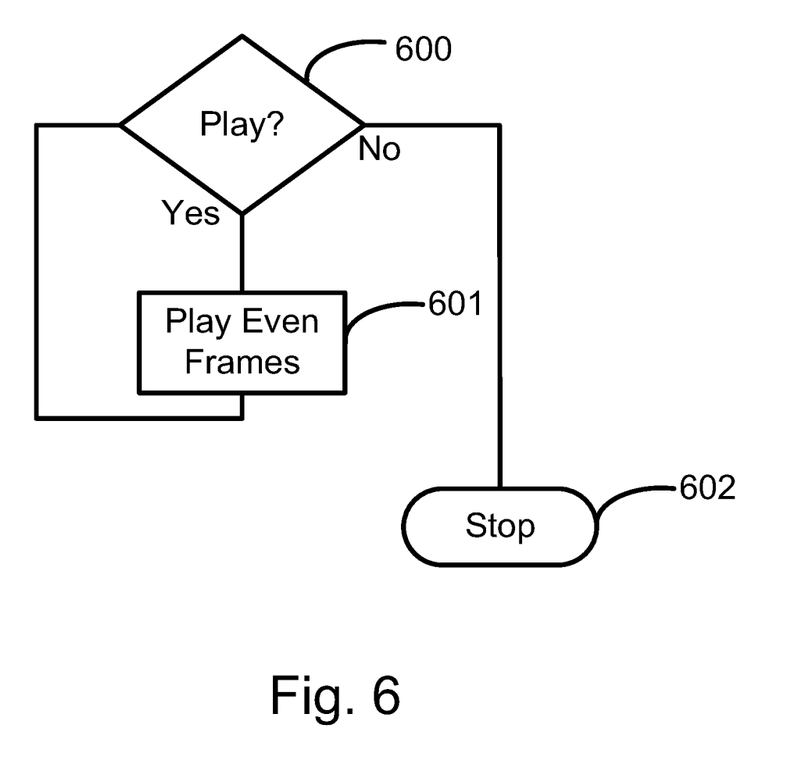
FIG. 6 is a flowchart illustrating the View playback process for the DermaMap skin-mapping device.

FIG. 6 illustrates how captured video is played back. In step 600, video playback is initiated. In step 601, the even video frames are displayed in order until they have all been displayed; once the last even frame is displayed, playback stops at step 602.

With the present invention, past skin image or images, based on position data in a new capture can be achieved. Also, a new skin capture based on position data in an existing image is possible. The system and method of the present invention can precisely determine the absolute position of where an image was taken of the skin as well as the sale of the image that was captured. As a result, changes to the condition of the skin over time for medical purposes can be tracked.

It would be appreciated by those skilled in the art that various changes and modifications can be made to the illustrated embodiments without departing from the spirit of the present invention. All such modifications and changes are intended to be covered by the appended claims.

What is claimed is:

1. A system for capturing, archiving and viewing high-resolution video images of the skin, comprising:
    a patient interface, comprising
        a platform;
        a patient position template, for directing a patient where to stand; and
        a position sensor interface;
    a handheld exam controller, comprising
        a display;
        a laser projector;
        a camera; and
        a position sensor; and
    an external storage device configured and arranged to archive the video images of the skin,
    wherein the handheld exam controller is configured and arranged to playback and display even numbered video image frames, of the video images, in order of capture by the camera, and
    wherein the handheld exam controller is configured and arranged to determine the scale of any skin lesions on the patient as a function of a captured illumination pattern in odd numbered video image frames, of the video images, and the size of elements in the illumination pattern is used to determine the scale of the video images and therefore determine the size of any skin lesions in the video images.

2. The system of claim 1, wherein the camera of the handheld exam controller has a fixed-focus.

3. The system of claim 1, wherein the handheld exam controller further includes a device configured and arranged to synchronize laser projector illumination with camera frame capture.

4. The system of claim 1, further comprising a device configured and arranged to determine the absolute position of the camera.

5. The system of claim 1, further comprising a device configured and arranged to retrieve a past skin image or images based on position data in a new capture.

6. The system of claim 1, further comprising a device configured and arranged to create a new skin capture based on position data in an existing image.

7. A system for capturing and analyzing high-resolution video images of the skin, comprising:
- a patient interface, comprising
  - a platform;
  - a patient position template, for directing a patient where to stand; and
  - a position sensor interface;
- a handheld exam controller, comprising
  - a laser projector;
  - a camera; and
  - a position sensor; and
- a storage device configured and arranged to archive the video images of the skin,
- wherein the handheld exam controller is configured and arranged to determine the scale of any skin lesions on the patient as a function of a captured illumination pattern in odd numbered video image frames, of the video images, and the size of elements in the illumination pattern is used to determine the scale of the video images and therefore determine the size of any skin lesions in the video images.

8. The system of claim 7, wherein the camera of the handheld exam controller has a fixed-focus.

9. The system of claim 7, further comprising a display for displaying the video images.

10. The system of claim 7, wherein the storage device is an external storage device.

11. The system of claim 7, wherein the handheld exam controller further includes a device configured and arranged to synchronize laser projector illumination with camera frame capture.

12. The system of claim 7, further comprising a device configured and arranged to determine the absolute position of the camera.

13. The system of claim 7, further comprising a device configured and arranged to retrieve a past skin image or images based on position data in a new capture.

14. The system of claim 7, further comprising a device configured and arranged to create a new skin capture based on position data in an existing image.

* * * * *